United States Patent [19]

Ishigami et al.

[11] Patent Number: 4,902,512
[45] Date of Patent: Feb. 20, 1990

[54] RHAMNOLIPID LIPOSOMES

[75] Inventors: Yutaka Ishigami; Yasuo Gama; Hitoshi Nagahora, all of Tsukuba; Tetsuhiko Hongu, Yokohama; Muneo Yamaguchi, Tsukuba, all of Japan

[73] Assignee: Director-General of Agency of Industrial Science and Technology and Shin-Etsu Chemical Co., Ltd., Japan

[21] Appl. No.: 145,040

[22] Filed: Jan. 19, 1988

[51] Int. Cl.$^4$ .................. A61K 37/00; A61K 37/22; A61K 9/66; B01J 13/02
[52] U.S. Cl. .................. 424/450; 428/402.2; 436/829
[58] Field of Search ......... 264/4.1, 4.3, 4.16, 264/4.6; 424/450; 428/402.2, 402.21

[56] References Cited

U.S. PATENT DOCUMENTS

| 4,247,411 | 1/1981 | Vanlerberghe et al. ......... 424/450 |
| 4,377,567 | 3/1983 | Geho ......................... 424/450 X |
| 4,394,149 | 7/1983 | Szoka, Jr. et al. ............. 427/213.3 X |
| 4,508,703 | 4/1985 | Redziniak et al. .............. 264/4.6 X |
| 4,515,736 | 5/1985 | Deamer ....................... 264/4.3 |
| 4,605,630 | 8/1986 | Kung et al. ................... 264/4.6 X |
| 4,619,794 | 10/1986 | Hauser ....................... 264/4.1 |

FOREIGN PATENT DOCUMENTS 0009842 4/1980 European Pat. Off. ......... 424/450

OTHER PUBLICATIONS

Shipley et al., 1973, Phase Behavior of... Diglycerides, BBA 311, 531–544.

Primary Examiner—Howard J. Locker
Assistant Examiner—John M. Covert
Attorney, Agent, or Firm—Lorusso & Loud

[57] ABSTRACT

A liposome having a bilayer structure composed of rhamnolipid A (2-O-α-decenoyl-α-L-rhamnopyranosyl-β-hydroxydecanoyl-β-hydroxydecanoic acid), rhamnolipid B (2-O-(2-O-α-decenoyl-α-rhamnopyranosyl)-α-L-rhamnopyranosyl-β-hydroxydecanoyl-β-hydroxydecanoic acid), or a salt thereof.

6 Claims, 1 Drawing Sheet

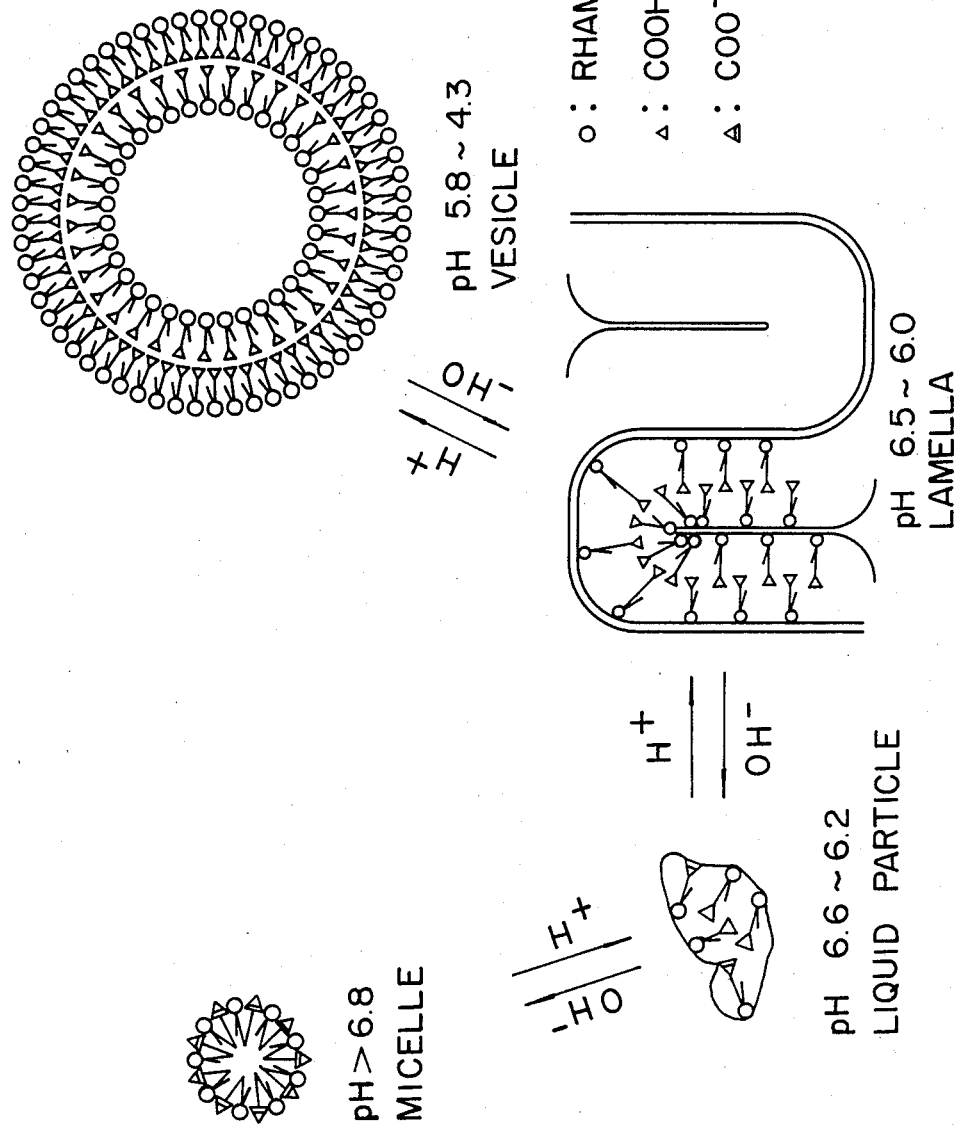

RHAMNOLIPID LIPOSOMES

BACKGROUND OF THE INVENTION

This invention relates to liposomes having a bilayer composed of rhamnolipid A, rhamnolipid B or a salt thereof.

In 1965 Bangham discovered that phosphatidylcholine forms liposomes (vesicles) which are microscopic particles with a diameter of 0.05-10 μm composed of biomembrane-like lipid bilayers. Thenceforth, a variety of studies have been made on applications of liposomes as a tool for studying the structures and functions of biological membranes, as a drug carrier for therapeutic purposes, and as a reaction medium for biological reactions. Liposomes have been also attempted to be used in the field of genetic engineering.

One problem associated with phosphatidylcholine liposomes is that they are unstable. That is, the liposomes are easily decomposed by heat or light and, therefore, they are susceptible to degradation during manufacture and storage. Further, the phospholipid liposomes are short in life and, therefore, they pose a particular difficulty of shelf conservation.

Liposomes formed of synthetic surfactants such as aerosol OT type anion dialkyl compounds and didodecylmethylammonium bromide are also known. However, these liposomes are not actually used for therapeutic or other applications for reasons of lack of safety, namely because of their skin irritating properties and their resistance to biological decomposition.

SUMMARY OF THE INVENTION

It is, therefore, an object of the present invention to provide novel liposomes which are composed of a naturally occurring substance, which have suitable affinity for biological organisms, which are safe and biologically decomposable and which are stable and have long service and shelf life.

Another object of the present invention is to provide liposomes of the above-mentioned type which are useful as microcapsules for drugs, proteins, nucleic acids, dyes and other compounds, as biomimetic models for biological membranes and as sensors for detecting pH variations.

In accomplishing the above object, there is provided in accordance with the present invention a liposome formed of rhamnolipid A, rhamnolipid B or a salt thereof.

In another aspect, the present invention provides a composition of matters, comprising an aqueous medium having a pH of 4.5-6.5, and liposomes formed of rhamnolipid A, rhamnolipid B or a salt thereof.

BRIEF DESCRIPTION OF THE DRAWINGS

Other objects, features and advantages of the present invention will become apparent from the detailed description of the invention which follows when considered in light of the accompanying drawing, in which:

the sole FIGURE is a schematic illustration of four types of the aggregated states of rhamnolipid molecules at different pH regions.

DETAILED DESCRIPTION OF THE INVENTION

The liposomes according to the present invention are composed of rhamnolipid A (2-O-α-decenoyl-α-L-rhamnopyranosyl-β-hydroxydecanoyl-β-hydroxydecanoic acid), rhamnolipid B (2-O-(2- O-α-decenoyl-α-rhamnopyranosyl)-α-L-rhamnopyranosyl-β-hydroxydecanoyl-β-hydroxydecanoic acid), or a salt thereof. Rhamnolipid A and rhamnolipid B have the following chemical structures:

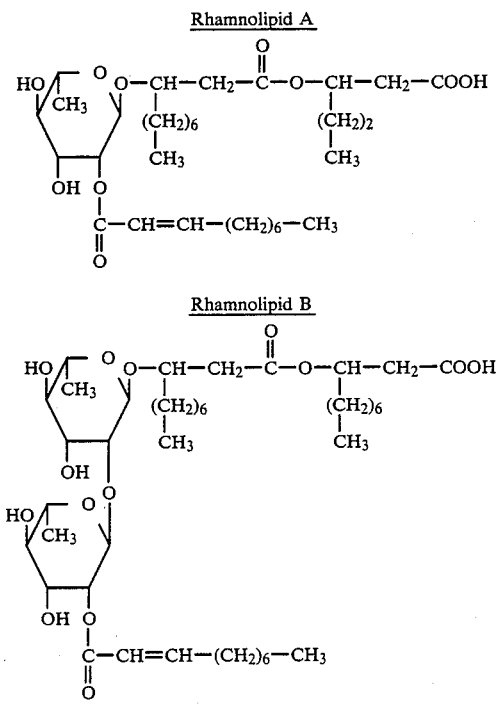

The derivatives of these rhamnolipids in which the carboxyl groups are converted into salts by neutralization, for example, with an alkali metal, alkaline earth metal, ammonia, morphorine and an alkylamine may be also used for the purpose of the present invention. These compounds are known per se and are used as a biosurfactant. In the rhamnolipids, the rhamnose residues and the carboxylic acid residues are hydrophilic while the two alkyl chains, i.e. the decenoyl residues and the β-hydroxypropionylpropionate resides having two heptyl groups are hydrophobic.

The liposomes may be prepared from the above rhamnolipids by any known method such as disclosed in an article "Cell Engineering", 2, 1136 (1983) (Hiroshi Kikuchi and Keizo Inoue). For example, the liposomes may be prepared by a method including the steps of forming a thin film of the rhamnolipid, and dispersing the film in an aqueous medium.

The formation of the thin film may be suitably effected by evaporating a solution of the rhamnolipid in an organic solvent, preferably a chloroform-methanol mixed solvent, to dryness in a round bottom or an eggplant type flask by means of a rotary evaporator, flash evaporator or the like. The formation of the suspension may be effected by adding the aqueous medium, preferably water or an aqueous buffer solution, into the flask to the inside wall of which the thin film deposits, and shaking the flask by means of a vortex mixer at a temperature above the phase transition temperature. The concentration of the rhamnolipid in the suspension is preferably 5-100 mM. When a buffer solution has been used for the formation of the rhamnolipid suspension, it is desired that aqueous solutions to be mixed later there-with should be isotonic with the buffer solution. The suspension may be subjected to a sonication treatment as desired.

The liposomes of the present invention may also be prepared by a method which includes the steps of dissolving a rhamnolipid in an organic solvent such as a chloroform/methanol 1:1 mixed solvent, admixing water with the organic solution, subjecting the admixture to a sonication treatment, and evaporating the organic solvent.

The liposomes according to the present invention may be suitably utilized as microcapsules for drugs, cosmetics, dyes or any other chemicals. Encapsulation may be effected in any known manner.

In the present specification, the term "liposome" is intended to refer to both closed and open vesicles. Open vesicle is also referred to as lamella. It has been found that the closed vesicles of rhamnolipids A and B are converted into the open vesicles by changing the pH. More particularly, at a pH in the range of 4.3–5.8 in which the carboxyl groups of the rhamnolipids are completely in the form of a free acid, the rhamnolipids form closed vesicles as schematically shown in FIGURE. At a pH in the range of 6.0–6.5, open vesicles (lamella) are formed. Further, as the aqueous phase becomes neutral, there are formed liquidus particles and finally micelle at a pH in the range of 6.8 or higher in which the carboxyl groups of the rhamnolipids are completely neutralized.

The following examples will further illustrate the present invention. Rhamnolipid A and rhamnolipid B used in the examples were obtained through biosynthesis by a fermentation method in which a hydrocarbon was used as a substrate. Namely, a hydrocarbon-decomposing bacterium BOP100 isolated from the natural world was cultured in an inorganic salt culture medium (pH: 7.0, nitrogen source: $NaN_{O3}$) containing 5% n-paraffin at 30° C. for 5 hours with shaking. The fermentation liquid thus obtained was subjected to an ether extraction under an acidic condition and then to a silica gel column chromatography using chloroform:methanol (95:5) as an elution liquid, thereby to isolate rhamnolipid A and rhamnolipid B having α-decenoic acid bonded thereto. The amounts of rhamnolipid A and rhamnolipid B produced were 3.4 g and 10.2 g, respectively, per 1 liter of the fermentation liquid. The yield of these rhamonolipids was 4.4 % based on the n-paraffin consumed. The structural elucidation of these rhamnolipids reveals that rhamnolipid A and rhamonolipid B have one rhamnose residue and two rhamnose residues, respectively. This suggests that rhamnolipid A is a precursor of rhamonolipid B. In these rhamnolipids, the sugar and terminal carboxylic acid moieties are hydrophilic groups while the decenoyl groups, hydroxydecanoic acid groups and their branched alkyl groups serve to function as hydrophobic groups. The thus obtained α-decenoic acid-carrying rhamnolipids were dissolved in water to obtain an 0.5 % aqueous solution and the solution adjusted to a pH of 7.0 by sodium hydroxide. The resulting solution was then subjected to a skin irritation test for 15 healthy women with pure water being used as a control. The results were evaluated in accordance with Japanese standard and did not reveal any skin irritation.

EXAMPLE 1

Rhamnolipid B (20 mg) was placed in a 100 ml round bottom flask and dissolved in 30 ml of a chloroform-methanol (2:1 vol/vol) mixed solvent. The flask was then connected to a rotary evaporator and the solvent was gradually evaporated to form a thin film of rhamnolipid B on the inside wall surface of the flask. The flask was placed in a desiccator for completely drying the film under a reduced pressure for 1 hour. Then, 3 ml of distilled water was added into the flask and the contents were agitated by means of a vortex mixer at 65° C. for 20 minutes to obtain a slightly turbid aqueous suspension. The suspension was caused to deposit onto a carbon grid previously treated for imparting hydrophilicity thereto and the resulting grid was immersed in a 2 % aqueous uranyl acetate solution for 2 minutes to effect negative staining. Upon analysis of the resulting grid by Hitachi HU-12A transmission electron microscope (magnification: x3000 to x150000), a multiplicity of vesicles (liposome) with a size of 0.1–3 μm were observed. When measured by a differential scanning calorimeter (mettler TA-3000) using an autoclave cell, the emulsion showed a strong endothermic peak at 31.6° C. The corresponding peak appeared at 23.1° C. in the case of the rhamnolipid B in a micelle state and at 84.7° C. in the case of that in an anhydrous state.

EXAMPLE 2

Rhamnolipid A (20 mg) was placed in a 100 ml flask and dissolved in 30 ml of a chloroform-methanol (2:1 vol/vol) mixed solvent. The solvent was then gradually evaporated by means of a flash evaporator to form a thin film of rhamnolipid A on the inside wall surface of the flask. After drying the film under a reduced pressure for 1 hour, 2 ml of distilled water was added into the flask and the contents were sufficiently agitated by means of a vortex mixer at a temperature higher by at least 10° C. than the phase transition temperature (28.4° C.) to obtain a translucent aqueous suspension. By analyzing the suspension by means of a transmission electron microscope (magnification: x2000 to x50000) after negative staining with phosphowolframic acid, vesicles with various shapes with a size of 0.1μ10 μm were observed. The formation of similar vesicles were also confirmed by an analysis with a fluorescence microscope (magnification: x400) using an oil soluble fluorescent dye (such as N-(5-fluorescenethiocarbamoyl) dipalmitoyl-L-phosphatidylethanolamine) during the formation of liposome by the vortex method for the incorporation of the dye into the lipid bilayer.

EXAMPLE 3

Example 1 was repeated using various phosphate buffer solutions (1/15 M, pH: 5.5 to 5.8, mixtures of 1/30 M $KH_2PO_4$ and 1/15 M $Na_2HPO_4$) in place of the distilled water for the formation of liposome. Microscopic analyses of the resulting suspensions revealed the formation of vesicles. When a buffer with a pH of 7.0 was used, however, the suspension of rhamnolipid B failed to form vesicles but became transparent and showed a surface tension (of 0% solution) of as low as 28 mN/m and an interfacial tension to kerosene of 3.2 mN/m.

The foregoing facts suggest that the aggregation state of rhamnolipid B freely reversibly varies with pH between vesicle-lamella-liquidus particle-micelle. In the aggregation state in which micelle is formed, the system has a high dispersion force, lathering force and penetration force depending on its concentration and has a greatly reduced surface tension and interfacial tension. That is, 3 ml of a 0.5 % aqueous solution of rhamnolipid B can completely emulsify 2 ml of kerosene. Even when the emulsion was maintained at 95° C. for 2 hours, the emulsion showed such a stability that the proportion of the emulsified phase in the oil layer still remained to be 96 %. The dispersion force was tested by a method including mixing 50 mg of finely divided, hardly dispersable, copper phthalocyanine blue with 20 ml of 0% aqueous solution of rhamnolipid B with agitation, allowing the dispersion to quiescently stand for 4 hours, collecting an upper liquid of the dispersion, diluting the collected liquid with water to a concentration 13.5 times that of the undiluted liquid, and measuring the turbidity of the diluted sample. The turbidity was 75 % in the case of 0.1 % aqueous rhamnolipid B solution and 46 % in the case of aerosol OT used as a control. The rhamnolipid solution was also found to be high in lathering force and penetration force (into cotton fabric and felt).

Rhamnolipid B (20 mg) was mixed with 1 mg of oil-soluble fluoresence dye N-(5-fluorescenethiocarbamoyl)-dipalmitoyl-L-phosphatidylethanolamine and a thin film of the mixture was formed on the inside surface of a 100 ml flask in the manner described above. After addition of 2 ml of a phosphate buffer with a pH 6.2), a vortex treatment was performed in the same manner as described above to give an aqueous suspension. The observation of the suspension by a fluoresence microscope (magnification: ×400) in B-excitation conditions reveals a uniformly oriented lamella structure. When a phosphate buffer with a pH of 6.4 was used in place of the buffer of pH 6.2, there were observed liquidus particles of indeterminate shapes by a fluorescence microscope. In view of the foregoing results, it is considered that rhamnolipid B in an aqueous liquid can form various aggregated molecular structures as shown in FIG. 1 depending upon the pH of the aqueous liquid.

EXAMPLE 4

Example 1 was repeated using various phosphate buffer solutions (1/15 M, pH: 5.5 to 5.8, mixtures of 1/30 M $KH_2PO_4$ and 1/15 M $Na_2HP_4$) in place of the distilled water and rhamnolipid A in place of rhamnolipid B for the formation of liposomes. Microscopic analyses of the resulting suspensions revealed the formation of vesicles. When a buffer with a pH of 7.0 was used, however, the suspension of rhamnolipid A failed to form vesicles but became transparent and showed a surface tension (of 0.1 % solution) of as low as 28 mN/m and an interfacial tension to kerosene of 0.2 mN/m.

The foregoing facts suggest that the aggregation state of rhamnolipid A reversibly varies with pH between visiclelamella-liquidus particle-micelle. In the aggregation state in which micelle is formed, the system has a high dispersion force, lathering force and penetration force depending on its concentration and has a greatly reduced surface tension and interfacial tension. That is, 0.5 % aqueous solution of rhamnolipid A was found to exhibit emulsifying power for kerosene of 73 % (SDS: 87 %). The dispersion force of 0.1 % aqueous solution of rhamnolipid A for copper phthalocyanine blue was 44 % (46 % in the case of aerosol OT and 33 % in the case of SDS). The rhamnolipid solution was also found to be high in lathering force and penetration force.

Rhamnolipid A (20 mg) was mixed with 1 mg of oil-soluble fluoresence dye N-(5-fluorescenethiocarbamoyl)- dipalmitoyl-L-phosphatidylethanolamine and a thin film of the mixture was formed on the inside surface of a 100 ml round bottom flask in the manner described above. After addition of 2 ml of a phosphate buffer (pH 6.2), a vortex treatment was performed in the same manner as described above to give an aqueous suspension. The observation of the suspension by a fluoresence microscope (magnification: x400) reveals a uniformly oriented lamella structure. When a phosphate buffer (pH: 6.4) was used in place of the buffer of pH 6.2, there were observed liquidus drops of indeterminate shapes by a fluorescence microscope. In view of the foregoing results, it is considered that rhamnolipid A in an aqueous liquid can form various aggregated molecular structures as shown in FIG. 1 which are depending upon the pH of the aqueous liquid.

EXAMPLE 5

Example 1 was repeated in the same manner as described except that the vortex mixing step was conducted in the presence of calsein. The calsein was found to be trapped in the aqueous phase within the vesicles.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

We claim:

1. A liposome formed of rhamnolipid A, rhamnolipid B or a salt thereof.

2. A liposome according to claim 1 in the form of a closed vesicle.

3. A liposome according to claim 1 in the form of an open vesicle.

4. A composition of matters, comprising an aqueous medium having a pH of 4.5-6.5, and liposomes formed of rhamnolipid A, rhamnolipid B or a salt thereof.

5. A composition according to claim 4, further comprising one or more compounds encapsulated in said liposomes.

6. A composition according to claim 5, wherein said compounds are selected from the group consisting of drugs, cosmetics and dyes.

* * * * *

UNITED STATES PATENT AND TRADEMARK OFFICE
CERTIFICATE OF CORRECTION

PATENT NO. : 4,902,512
DATED : February 20, 1990
INVENTOR(S) : ISHIGAMI et al

It is certified that error appears in the above-identified patent and that said Letters Patent is hereby corrected as shown below:

IN THE CLAIMS:

Column 6, line 48, delete "matters, -" and insert --matter--.

Signed and Sealed this

Twenty-sixth Day of March, 1991

Attest:

HARRY F. MANBECK, JR.

*Attesting Officer*      *Commissioner of Patents and Trademarks*